United States Patent [19]
Simonson

[11] Patent Number: 5,643,263
[45] Date of Patent: Jul. 1, 1997

[54] SPINAL IMPLANT CONNECTION ASSEMBLY

[76] Inventor: Peter Melott Simonson, 770 Claughton Island Dr., Suite 414, Miami, Fla. 33131

[21] Appl. No.: 515,289

[22] Filed: Aug. 14, 1995

[51] Int. Cl.[6] .................................................. A61B 17/56
[52] U.S. Cl. .............................. 606/61; 606/72; 606/73
[58] Field of Search ................................. 606/60, 61, 69, 606/70, 71, 72, 73, 54, 59

[56] References Cited

U.S. PATENT DOCUMENTS

| | | |
|---|---|---|
| 3,317,225 | 5/1967 | Cooper . |
| 4,611,582 | 9/1986 | Duff . |
| 4,614,452 | 9/1986 | Wang . |
| 4,738,252 | 4/1988 | Friddle et al. . |
| 4,827,918 | 5/1989 | Olerud . |
| 5,002,542 | 3/1991 | Frigg . |
| 5,013,085 | 5/1991 | Craig . |
| 5,041,112 | 8/1991 | Mingozzi et al. . |
| 5,047,029 | 9/1991 | Aebi et al. ................................ 606/61 |
| 5,053,034 | 10/1991 | Olerud ..................................... 606/60 |
| 5,057,109 | 10/1991 | Olerud . |
| 5,092,867 | 3/1992 | Harms et al. . |
| 5,108,395 | 4/1992 | Laurain . |
| 5,108,397 | 4/1992 | White . |
| 5,190,390 | 3/1993 | Ming-Tai . |
| 5,254,118 | 10/1993 | Mirkovic . |
| 5,261,909 | 11/1993 | Sutterlin et al. . |
| 5,312,404 | 5/1994 | Asher et al. . |
| 5,320,623 | 6/1994 | Pennig . |
| 5,344,422 | 9/1994 | Frigg . |
| 5,376,090 | 12/1994 | Pennig . |
| 5,423,818 | 6/1995 | Van Hoeck et al. . |
| 5,443,465 | 8/1995 | Pennig . |
| 5,443,467 | 8/1995 | Biedermann et al. . |
| 5,443,515 | 8/1995 | Cohen et al. . |

*Primary Examiner*—Michael Buiz
*Assistant Examiner*—Mark S. Leonardo

[57] ABSTRACT

A connection assembly for connecting a spinal implant rod to a spinal implant bolt includes a rod connecting member having an aperture for receiving a portion of the rod and a bolt connecting member having an aperture for receiving a portion of the bolt. The rod connecting member and bolt connecting member are rotatably engaged to one another. A rod interface washer is positioned over a portion of the rod connecting member, and a bolt interface washer is positioned over a portion of the bolt connecting member. The rod interface washer and bolt interface washer are moveable in part between the rod connecting member and the bolt connecting member, the rod connecting washer being fixed against rotation relative to the rod connecting member and the bolt interface washer being fixed against rotation relative to the bolt interface washer. Structure extendable into at least one of the apertures is provided, so as to urge one of the rod and bolt toward the other, and to cause the washers to be pressed together between the rod and the bolt, preventing rotation of the rod interface washer and rod connecting member relative to the bolt interface washer and bolt connecting member, and securing the rod to the bolt.

7 Claims, 2 Drawing Sheets

SPINAL IMPLANT CONNECTION ASSEMBLY

FIELD OF THE INVENTION

This invention relates generally to a spinal implant assembly, and more particularly to a spinal implant connection assembly.

BACKGROUND OF THE INVENTION

Spinal implant systems provide a rod for supporting the spine and properly positioning components of the spine for various treatment purposes. Bolts or screws are typically secured into the vertebrae for connection to the supporting rod. These bolts must frequently be positioned at various angles due to the anatomical structure of the patient, the physiological problem, and the preference of the physician. It is difficult to provide secure connection between the spinal support rod and these connecting bolts at various angles, and where there are differing distances between the rod and bolts and different heights relative to these components.

SUMMARY OF THE INVENTION

It is an object of the invention to provide a connection assembly which will securely engage a spinal support rod to connecting bolts.

It is a further object of the invention to provide a connection assembly which will provide for engagement of the spinal support rod to the connecting bolts where the connecting bolts are at a variety of angles relative to the vertical, taken when the patient is lying down.

It is yet another object of the invention to provide a connection assembly which will allow connection between a spinal support rod and connecting bolts at a variety of vertical and horizontal distances between the rod and bolts.

These and other objects are accomplished by a connection assembly for connecting a spinal implant rod to a spinal implant bolt which includes a rod connecting member having an aperture for receiving a portion of the rod and a bolt connecting member having an aperture for receiving a portion of the bolt. The rod connecting member and bolt connecting member are rotatably engaged to one another. A rod interface washer is positioned over a portion of the rod connecting member, and a bolt interface washer is positioned over a portion of the bolt connecting member. The rod interface washer and bolt interface washer are moveable in part between the rod connecting member and the bolt connecting member, the rod connecting washer being fixed against rotation relative to the rod connecting member and the bolt interface washer being fixed against rotation relative to the bolt interface washer. Structure extendable into at least one of the apertures is provided, so as to urge one of the rod and bolt toward the other, and to cause the washers to be pressed together between the rod and the bolt, preventing rotation of the rod interface washer and rod connecting member relative to the bolt interface washer and bolt connecting member, and securing the rod to the bolt.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE PREFERRED EMBODIMENTS

Figure 1:
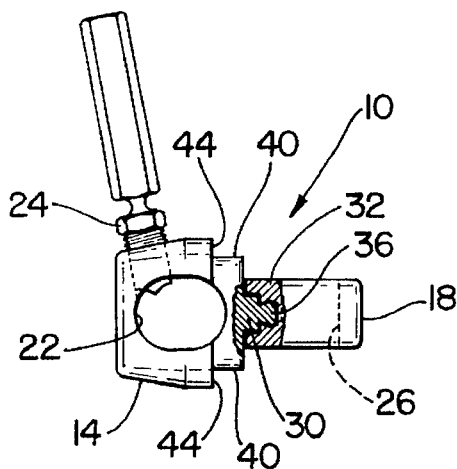
FIG. 1 is a front elevation of a rod connecting member and bolt connecting member according to the invention, partially in phantom.
Figure 2:
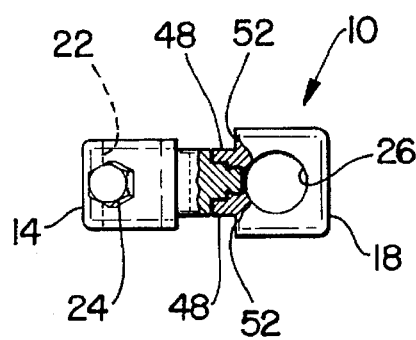
FIG. 2 is a plan view.

There is shown in FIGS. 1–2 a spinal implant connection assembly 10 according to the invention. The swivel assembly connection 10 comprises a rod connecting member 14 and a bolt connecting member 18. The rod connecting member 14 has an aperture 22 for receiving a rod in a spinal implant system. Structure for urging the rod within the aperture 24, such as the set screw 24, is provided through a suitable threaded opening in the rod connecting member 14 so as to be extendable into the aperture 22. The bolt connecting member 18 has an aperture 26 for receiving a bolt or screw of a spinal implant system.

The rod connecting member 14 and bolt connecting member 18 are attached by a rotatable connection. The rotatable connection can be of any suitable design. It is preferable that the swivel connection have a snap-together construction to facilitate the assembly of the final device. In one suitable design, the rod connecting member 14 can have a male protrusion 30 and the bolt connecting member 18 can have a corresponding female cavity formed in a neck 32. A flared end portion 36 of the male protrusion 30 can be provided to cooperate with a corresponding portion of the female cavity to provide snap-in engagement. The male protrusion 30 is preferably symmetrical about its long axis to facilitate rotation in the female cavity, and will thereby provide a swivel connection between the rod connecting member 14 and the bolt connecting member 18.

Alternatively, the male and female connections could be provided by a threaded member, such as a screw, and a threaded opening in one of the rod connecting member 14 and the bolt connecting member 18. The screw would extend through an opening in one of the rod connecting member 14 and bolt connecting member 18 to connect to the threaded opening in the other member, so as to rotatably engage the two members together.

The rod connecting member 14 can have a washer seat portion 40. A seat that is substantially rectangular in cross section is currently preferred, but the seat 40 can be of any suitable shape. A washer stop surface 44 can be provided by an enlarged portion of the rod connecting member 14. The bolt connecting member can have a washer seat 48 and a similar washer stop surface 52.

Figures 3, 4, 5:
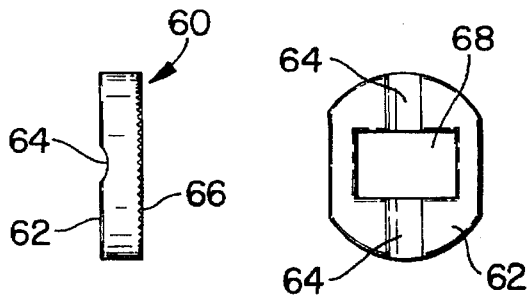
FIG. 3 is a front elevation of an interface washer according to the invention.
FIG. 4 is a side elevation.
FIG. 5 is an opposite side elevation.

An interface washer 60 according to the invention is shown in FIGS. 3–5. The interface washer can be any of several suitable shapes, including the semi-oval shape that is depicted. One surface of the interface washer 60 has an engagement surface 62, which preferably has an engagement groove 64 for engaging a cylindrical rod, bolt or screw surface. The engagement groove 64 runs substantially diametrically through the oval washer. A central opening 68 in the washer corresponds in shape to the cross-sectional shape of the respective washer seat to which it is engaged, whether the washer seat 40 of the rod connecting member 14 or the washer seat 48 of the bolt connecting member 18. In the currently preferred embodiment, the corresponding openings and washer seats are of substantially rectangular shape, although this shape could vary and be of varying size, and could also be different for the washer seat 40 of the rod connecting member 14 and the washer seat 48 of the bolt connecting member 18.

The interface washer 60 has a washer connection surface 66 opposite to the engagement surface 62. The washer connection surface 66 preferably includes structure for facilitating the engagement of the washer against rotational movement relative to another interface washer against which it is pressed. This engagement structure is preferably a plurality of variable angle ridges 72 which radiate from the rotational center of the interface washer 60, as will be explained below.

Figure 6:
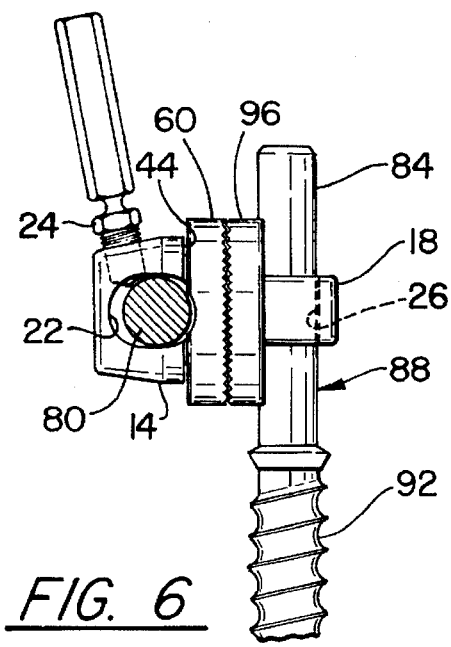
FIG. 6 is a front elevation, partially in cross-section and partially in phantom, of a connection assembly according to the invention in a positioning mode.
Figure 7:
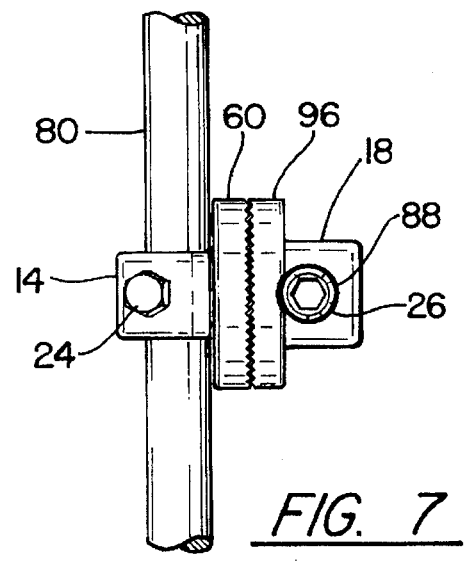
FIG. 7 is a plan view, partially broken away and partially in phantom.

The complete rotatable connection assembly 10 is shown in FIGS. 6–7. A rod 80 is positioned in the aperture 22 of the rod connecting member 14. A post 84 of a bolt 88 that is connected to a screw portion 92 is positioned through the aperture 26 of the bolt connecting member 18. It will be appreciated that the screw 92 is typically oriented somewhat vertically into the spine when the patient is lying horizontally. The rod 80 extends somewhat horizontally along the length of the spine of the patient, again when the patient is lying.

Two interface washers 60 are provided with the connection assembly of the invention. A first interface washer 60 is provided over the washer seat 40 of the rod connecting member 14. A second interface washer 96, preferably similar in construction to the interface washer 60, is positioned over the washer seat 48 of the bolt connecting member 18. The washer connection surfaces 66 of each washer face one another in the completed assembly. In the present embodiment, the bolt interface washer 96 is substantially identical to the rod interface washer 60, and includes an engagement groove 64, an opening 68, and variable angle surfaces 72. The variable angle surfaces 72 of the rod interface washer 60 and the bolt interface washer 96 face one another in the assembled swivel connection assembly. This permits mutual engagement of the rod interface washer 60 and the bolt interface washer 96.

The rod interface washer 60 and bolt interface washer 96 are oriented substantially 180° to one another because of the orientation of the rod connecting member 14 and bolt connecting member 18. The width of the interface washers 60 and 96 is less than the distance between the respective washer stop surface 44 of the rod connecting member 14 and the washer stop surface 52 of the bolt connecting member 18. There is therefore some freedom of movement of the interface washers 60 and 96 between to the rod connecting member 14 and bolt connecting member 18. Also, because the variable angle surfaces 72 are non-engaged, the rod connecting member 14 and rod interface washer 60 can rotate freely with respect to the bolt connecting member 18 and the bolt interface washer 96.

The aperture 22 of the rod connecting member 14 and aperture 26 of the bolt connecting member 18 are larger in dimension than the cross section of the rod 80 and bolt 88, such that movement of each within the respective aperture is possible. The flexibility of the invention in making a connection between the rod 80 and a plurality of bolts 88 is provided because the swivel assembly can be moved up and down over the portion 84 and horizontally over the rod 80, as can be seen from FIGS. 6–7. The rod 80 and bolt 88 can be in differing angular positions, because the rod connecting member 14 and bolt connecting member 18 can rotate relative to each other. Finally, the linear distance between the rod 80 and bolt 88 can be adjusted because of the variability provided by the apertures 22 and 26. Also, different sizes of spinal implant connection assemblies 10 according to the invention can be provided, and with different thicknesses of interface washers 60 and 96, such that differing distances between the rod 80 and bolt 88 can be accommodated.

Figure 8:
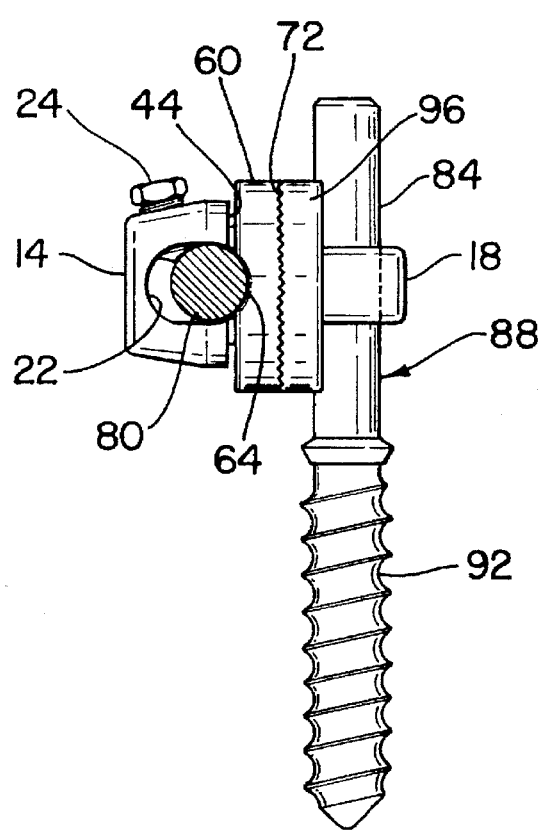
FIG. 8 is a front elevation, partially in cross section and partially in phantom, of a connection assembly according to the invention in a secured mode.
Figure 9:
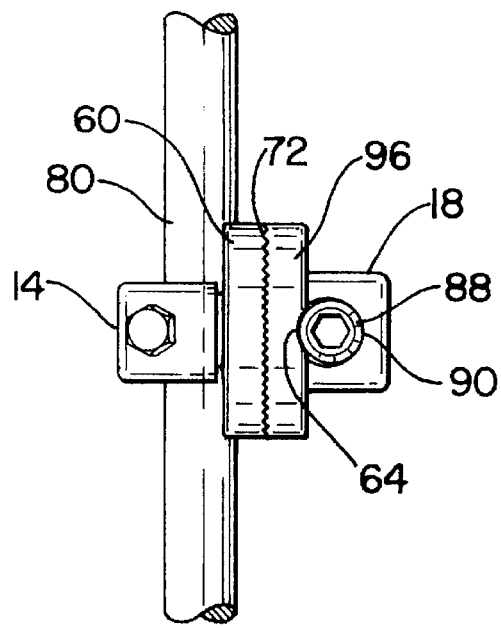
FIG. 9 is a plan view, partially broken away and partially in phantom.

The manner of connection of the spinal implant connection assembly 10 according to the invention to the rod 80 and the bolt 88 is depicted in FIGS. 8–9. When the rod connecting member 14 and bolt connecting member 18 have been properly positioned over the rod 80 and bolt 88, it is necessary to tighten the connection to retain this position. This is accomplished by use of the set screw 24. The set screw 24 is threaded into the aperture 22 (FIG. 8) where it contacts the side of the rod 80 and forces the rod 80 toward the bolt connecting member 18. The rod 80 contacts the rod interface washer 60, and preferably engages the engagement groove 64 as previously described. This will force the rod interface washer 60 against the bolt interface washer 96. The variable angle surfaces 72 of each will engage to prevent further rotation of the rod connecting member 14 and bolt connecting member 18 relative to one another, because the rod interface washer 60 and bolt interface washer 96 are fixed relative to the respective rod connecting member 14 and bolt connecting member 18. The assembly becomes unitary and cannot swivel when they are engaged. As the set screw 24 is threaded further into the cavity 22, the rod interface washer 60 and bolt interface washer 96 are forced further toward the bolt 88. The bolt 88 is engaged by the bolt interface washer 96, preferably by an engagement groove 64. This will force the bolt 88 against a lateral surface 90 of the aperture 26 to secure the bolt 88 in place. The entire assembly will thereby become locked against movement. Adjustments can be made by loosening the set screw 24 and then re-tightening the set screw when the preferred position has been located.

The invention is capable of taking a number of specific forms without departing from the spirit or essential attributes thereof. Accordingly, reference should be had to the following claims, rather than the foregoing specification, as indicating the scope of the invention.

I claim:

1. A connection assembly for connecting a spinal implant rod to a spinal implant bolt, the assembly comprising:

a rod connecting member having an aperture for receiving a portion of the rod;

a bolt connecting member having an aperture for receiving a portion of the bolt, the rod connecting member and the bolt connecting member being engaged to one another so as to be rotatable about a connection axis;

a rod interface washer positioned over a portion of the rod connecting member;

a bolt interface washer positioned over a portion of the bolt connecting member, the rod interface washer and bolt interface washer being moveable in part between the rod connecting member and the bolt connecting member, the rod connecting washer being fixed against rotation relative to the rod connecting member and the bolt interface washer being fixed against rotation relative to the bolt connecting member; and structure extendable into the aperture of at least one of the rod connecting member and the bolt connecting member, so as to urge one of the rod and the bolt toward the other, whereby at least one of the rod interface washer and the bolt interface washer will move substantially along said connection axis and will be pressed together between the rod and the bolt, preventing rotation of the rod interface washer and the rod connecting member relative to the bolt interface washer and the bolt connecting member, and securing the rod to the bolt.

2. A connection assembly for connecting a spinal implant rod to a spinal implant bolt, the assembly comprising:

a rod connecting member having an aperture for receiving a portion of the rod;

a bolt connecting member having an aperture for receiving a portion of the bolt, the rod connecting member and the bolt connecting member being rotatably engaged to one another;

a rod interface washer positioned over a portion of the rod connecting member;

a bolt interface washer positioned over a portion of the bolt connecting member, the rod interface washer and bolt interface washer being moveable in part between the rod connecting member and the bolt connecting member, the rod connecting washer being fixed against rotation relative to the rod connecting member and the bolt interface washer being fixed against rotation relative to the bolt connecting member; and structure extendable into the aperture of at least one of the rod connecting member and the bolt connecting member, so as to urge one of the rod and the bolt toward the other, whereby the rod interface washer and the bolt interface washer will be pressed together between the rod and the bolt, preventing rotation of the rod interface washer and the rod connecting member relative to the bolt interface washer and the bolt connecting member, and securing the rod to the bolt;

the interface washers having interengagement structure on a surface thereof such that, when pressed together, the interengagement structure will facilitate the engagement of the washers to one another against rotational movement relative to one another.

3. A connection assembly for connecting a spinal implant rod to a spinal implant bolt, the assembly comprising:

a rod connecting member having an aperture for receiving a portion of the rod;

a bolt connecting member having an aperture for receiving a portion of the bolt, the rod connecting member and the bolt connecting member being rotatably engaged to one another;

a rod interface washer positioned over a portion of the rod connecting member;

a bolt interface washer positioned over a portion of the bolt connecting member, the rod interface washer and bolt interface washer being moveable in part between the rod connecting member and the bolt connecting member, the rod connecting washer being fixed against rotation relative to the rod connecting member and the bolt interface washer being fixed against rotation relative to the bolt connecting member; and structure extendable into the aperture of at least one of the rod connecting member and the bolt connecting member, so as to urge one of the rod and bolt toward the other, whereby the rod interface washer and the bolt interface washer will be pressed together between the rod and the bolt, preventing rotation of the rod interface washer and the rod connecting member relative to the bolt interface washer and the bolt connecting member, and securing the rod to the bolt;

the interface washers having interengagement structure on a surface thereof such that, when pressed together, the interengagement structure will facilitate the engagement of the washers to one another against rotational movement relative to one another, said interengagement structure comprising variable angle surfaces.

4. The connection assembly of claim 1, wherein each of the rod connecting member and the bolt connecting member comprises a washer seat and washer stop for permitting sliding movement of the respective interface washer over a portion of the respective aperture, said stop surface preventing removal of the interface washer from the respective connecting member.

5. The connection assembly of claim 1, wherein the rod connecting member and the bolt connecting member are rotationally engaged by corresponding male protrusion and female cavity portions.

6. The connection assembly of claim 1, wherein said interface washers comprise an engagement groove.

7. A method for connecting a rod to a bolt in a spinal implant system for a patient, comprising the steps of:

providing spinal implant rod and at least one connecting bolt;

providing a connection assembly comprising a rod connecting member having an aperture for receiving a portion of the rod, a bolt connecting member having an aperture for receiving a portion of the bolt, the rod connecting member and the bolt connecting member being rotatably engaged to one another; a rod interface washer positioned over a portion of the rod connecting member; a bolt interface washer positioned over a portion of the bolt connecting member, the rod interface washer and the bolt interface washer being moveable in part between the rod connecting member and the bolt connecting member, the rod connecting washer being fixed against rotation relative to the rod connecting member and the bolt interface washer being fixed against rotation relative to the bolt interface washer; and structure extendable into the aperture of at least one of the rod connecting member and the bolt connecting member, so as to urge one of the rod and bolt toward the other;

positioning the rod connecting member over the desired portion of the rod;

positioning the bolt connecting member over the desired portion of the bolt;

extending said extendable structure so as to urge one of the rod and the bolt toward the other, whereby the rod interface washer and bolt interface washer will be pressed together between the rod and the bolt, preventing rotation of the rod interface washer and the rod connecting member relative to the bolt interface washer and the bolt connecting member, and securing the rod to the bolt.

* * * * *